United States Patent [19]
Bard et al.

[11] Patent Number: 5,811,514
[45] Date of Patent: Sep. 22, 1998

[54] INTEGRIN BLOCKING MOLECULE

[75] Inventors: Frederique Bard, San Francisco; Theodore A. Yednock, Fairfax; Pamela S. Keim, San Mateo, all of Calif.

[73] Assignee: Athena Neurosciences, South San Francisco, Calif.

[21] Appl. No.: 457,192

[22] Filed: Jun. 1, 1995

Related U.S. Application Data

[62] Division of Ser. No. 104,210, Aug. 9, 1993, abandoned.

[51] Int. Cl.[6] .............................. C07K 5/00; C07K 7/00; C07K 17/00
[52] U.S. Cl. .................... 530/324; 530/412; 536/22.1; 536/23.1; 536/23.5; 435/69.1; 435/69.6; 435/71.1; 435/71.2
[58] Field of Search .................. 530/350, 300, 530/324, 412; 536/22.1, 23.1, 23.5; 435/69.1, 69.6, 71.1, 71.2

*Primary Examiner*—Sheela Huff
*Attorney, Agent, or Firm*—Townsend & Townsend & Crew

[57] ABSTRACT

The invention relates to protein or polypeptide compositions capable of inhibiting leukocyte adhesion to, and transmigration across endothelial tissue. The invention further relates to nucleic acid molecules encoding such peptides, pharmaceutical compositions containing such peptides and methods of using such polypeptides.

7 Claims, 2 Drawing Sheets

FIGURE 1

Phe-Phe-Asp-Glu-Pro-Asn-Pro-Gly-Val-Thr-Ile-X-Ser-
Asp-Pro-Ser-Lys-Gln-Glu-(Glu)-X-Lys-X-Leu-X-

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 25 amino acids
( B ) TYPE: amino acid
( D ) TOPOLOGY: linear ( i i ) MOLECULE TYPE: peptide ( i i i ) HYPOTHETICAL: NO ( x i ) SEQUENCE DESCRIPTION: SEQ ID NO:1:

```
Phe  Phe  Asp  Glu  Pro  Asn  Pro  Gly  Val  Thr  Ile  Xaa  Ser  Asp  Pro  Ser
1                  5                       10                       15

Lys  Gln  Glu  Glu  Xaa  Lys  Xaa  Leu  Xaa
               20                  25
```

( 2 ) INFORMATION FOR SEQ ID NO:2:

( i ) SEQUENCE CHARACTERISTICS:
( A ) LENGTH: 72 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

```
TTYTTYGAYG  ARCCNAAYCC  NGGNGTNACN  ATHNNNWSNG  AYCCNWSNAA  RCARGARGAR        60

NNNAARNNNY  TN                                                               72
```

INTEGRIN BLOCKING MOLECULE

This is a Division of application Ser. No. 08/104,210 filed Aug. 9, 1993 abandoned.

BACKGROUND OF THE INVENTION

Increased adherence of polymorphonuclear neutrophils (PMNs or neutrophils) to endothelium is generally recognized to be a distinguishing feature of acute inflammatory response. The fundamental mechanism of neutrophil action in such inflammatory response has been established as beginning with initial adherence of the neutrophils to the vascular endothelium of the vessel wall nearest the injury, in response to certain chemoactivating signals (Harlan J M (1985) *Blood* 65: 513). The neutrophils remain adhered to the vascular wall until they migrate through the wall into the surrounding tissue. The accumulation of neutrophils in local tissue results in acute inflammation. Once in the surrounding tissue, the neutrophils can complex with target cells for recirculation to the lymphoid organs and/or produce an oxidative burst response leading to the production of free radicals, such as superoxide and peroxides. Such free radicals are highly reactive and produce damage to cells and biological macromolecules in the immediate area.

Although neutrophils serve an important immunological function, the infiltration of large numbers of neutrophils and other leukocytes has been shown to have a causal relationship to injury of the endothelial tissue in the area of the inflammatory response. In vital tissues, such as the brain, such an injury can have grave consequences. For example, in acute inflammatory diseases, such as a stroke or other cerebral trauma, large numbers of neutrophils infiltrate and can damage the tissues of the brain. Similarly, in chronic inflammatory diseases, such as multiple sclerosis, viral or bacterial infections (e.g., meningitis, encephalitis), large numbers of lymphocytes and monocytes infiltrate the brain parenchyma. The damage caused to neurons by the transmigration of large numbers of such inflammatory cells can be irreversible. It would thus be desirable to be able to inhibit leukocyte transmigration across endothelial tissue, and thus prevent or inhibit the associated tissue damage.

Specific compositions and methods have been described which attempt to reduce leukocyte transmigration across endothelial tissues. One strategy for attenuating an inflammatory process is to prevent the initial adhesion of leukocytes to vasular endothelium by competitive inhibition of cell surface receptors which mediate adhesion between leukocytes and endothelial cells (Springer T A (1990) *Nature* 346: 425; Tuomanen et al. (1989) *J. Exp. Med* 170: 959). These compositions generally include antibodies specific to adhesion-associated macromolecules present on either the leukocyte or the endothelial tissue, or non-protein small molecules (e.g., complex carbohydrates) which interfere with the adhesion or transmigration of the leukocyte through the endothelium. The described antibodies and small molecules can be specific for either the leukocyte or the particular endothelial cell type.

Administration of antibodies to the various subunits of the CD-18 complex on the surface of neutrophils can inhibit neutrophil adhesion to endothelial tissues following reperfusion of ischemic tissues. Inhibition of this adhesion prevents neutrophil accumulation, which results in a reduction of the tissue injury generally associated with such accumulation.

For example, Hill et al. (1992) *Surgery* 112: 166 reported that after ischemic tissues such as skeletal muscle and intestinal tissues are reperfused, systemic levels of chemoactivating factors are elevated. These factors lead to systemic activation of neutrophils, resulting in upregulation of adhesion integrins on their surface. The increased adhesion of neutrophils to the endothelium of various organs in turn leads to increased injury to the endothelial tissue of these organs. Antibodies to the CD11b α-subunit or the CD-18 β-subunit of the CD-18 complex, were shown to markedly inhibit neutrophil adhesion to endothelium. This inhibition in turn, was shown to prevent neutrophil-mediated lung and liver injury which generally followed reperfusion of ischemic intestinal tissues.

Similarly, Tanaka et al. (1993) *Circulation* 87: 526 reported that antibodies to the CD-18 β-subunit reduced the number of neutrophils that accumulated in post-ischemic myocardium during the first 3 hours of reperfusion after a 90 minute episode of coronary occlusion.

Tuonamen et al. (1989) op.cit reported that anti-β2 antibodies successfully reduced neutrophil accumulation in brain tissues of rabbits suffering from bacterial meningitis.

Clark et al. (1991) *J. Neurosurg*. 75: 623 reported that antibodies to an intercellular adhesion molecule (ICAM) on endothelium which is known to interact with the CD-18 complex can inhibit the adhesion of polymorphonuclear lymphocytes and their subsequent transmigration in central nervous system (CNS) ischemic tissue. Treatment with these antibodies reportedly resulted in reduced CNS injury when ischemic CNS tissues were reperfused.

Unfortunately, antibodies are large molecules that are expensive to produce and may eventually induce an antiantibody response which can compromise their activity, among other adverse effects.

Certain small molecules have also been reported that exhibit the ability to inhibit or prevent the onset of an acute inflammatory response. Burch et al. (1991) *Proc. Natl. Acad. Sci. (USA)* 88: 355 reported that N-(Fluorenyl-9-methoxycarbonyl) amino acids, termed "leumedins", inhibited arachidonic acid-induced edema in mouse ears and the recruitment/accumulation of neutrophils in response to arachidonic acid treatment. Carbohydrates which competitively bind to adhesion molecules present on the surfaces of endothelial cells or leukocytes and thereby block the availability of binding sites on the adhesion molecules for mediating inflammation-related intercellular adhesion have also been proposed. Unfortunately, the synthesis of such carbohydrates is expensive and difficult, and their clinical efficacy and utility remains unproven.

Thus, there exists a need in the art for compounds which inhibit leukocyte binding to endothelium ("pavementing") and/or subsequent transmigration and extravasation into tissue interstitial spaces. The present invention provides such compositions and methods for their production and usage.

Ribiero et al. (1990) *Exp. Parasitol*. 70: 382 report that the saliva of female ticks (*Ixodes dammini*) inhibits certain neutrophil functions, such as anaphylatoxin-induced aggregation, FMLP-induced granule enzyme secretion, zymosan-induced superoxide secretion, and phagocytosis of *Borrelia burgdorferi* spirochetes. Ribiero et al. (1986) *Exp. Parasitol*. 62: 292 indicate that tick saliva contains a carboxypeptidase with specificity for terminal basic amino acids. Ribiero et al. (1985) *J. Exp. Med*. 161: 332 report that saliva of the tick *Ixodes dammini* inhibits platelet aggregation and contains antipyrase and kininase activities. WO93/09231 discloses a thrombin-inhibiting 26 kD protein isolated from ticks. Karczewski et al. (1993) *Thrombosis and*

*Hemostasis* 69: 975 report isolation from the tick *Ornithodoros moubata* of a 6 kD platelet fibrinogen receptor antagonist protein.

SUMMARY OF THE INVENTION

The present invention provides novel polypeptides derived from the salivary glands of ticks. Said polypeptides are termed "tick-derived anti-inflammatory proteins" and produce effective inhibition of cell adhesion mediated via cell surface adhesion proteins such as integrins (e.g., $\beta_1$ integrins, $\beta_2$ integrins); also see, e.g., *Adhesion: Its Role in Inflammatory Disease*, Harlan J M and Liu D Y, eds. W. H. Freeman and Co., New York, 1992). Generally, tick-derived anti-inflammatory polypeptides can inhibit adhesion of leukocytes (e.g., neutrophil adhesion to endothelial cells) and/or inhibit transmigration of leukocytes cross endothelium. By inhibiting adhesion and/or transmigration of leukocytes the polypeptides of the present invention can be used to inhibit an inflammatory response and reduce the consequent tissue damage, especially of central nervous system tissues (e.g., brain parenchyma), and the like. The term "tick-derived anti-inflammatory protein" encompasses analogous proteins present in other insect species (i.e., non-tick species) and simply reflects that the family of anti-inflammatory proteins has been initially identified in ticks. A "cognate tick-derived anti-inflammatory protein" as used herein refers to a protein sequence that is evolutionarily and functionally related between species, wherein the sequences and structures of two proteins indicate that they are highly homologous and both proteins possess similar biological activities. Thus, with reference to the 4 kD or 20 kD proteins described herein from Ixodes or Amblyomma, the cognate protein in another species (e.g., another tick species) is the protein which has the greatest degree of sequence identity to the Ixodes or Amblyomma protein and which exhibits inhibition of integrin-mediated adhesion. Such cognate proteins are typically identified by identifying the encoding polynucleotide sequences in the other species by, for example, cloning methods employing low stringency nucleic acid hybridization using a polynucleotide probe (e.g., degenerate oligonucleotide probe(s) or a cDNA or genomic gene clone).

It is an object of the present invention to provide compositions comprising substantially pure polypeptides, derivatives, fragments, or analogues thereof, and formulations thereof which are capable of inhibiting adhesion of leukocytes to endothelial cells and/or inhibiting transmigration of leukocytes across the endothelium. Preferably, the polypeptides of the present invention will inhibit neutrophil adhesion to endothelial cells and transmigration across endothelial tissues. This invention further provides polynucleotides encoding such polypeptides, expression vectors comprising such polynucleotide sequences, cells capable of expressing the polynucleotide sequences, and methods for culturing the cells to produce the polypeptides.

In one embodiment, a native protein having detectable activity for inhibiting neutrophil transmigration has a molecular weight of approximately 20 kD as determined by gel filtration chromatography is provided. Biologically active fragments of the 20 kD protein are also provided.

In one embodiment, a native protein having a molecular weight of approximately 4 kD as determined by gel filtration chromatography is provided. Biologically active fragments of the 4 kD protein are also provided.

In one aspect of the invention, a substantially pure polypeptide comprising a biologically active polypeptide segment of a tick-derived anti-inflammatory protein inhibits leukocyte adhesion and/or transmigration across endothelium. Preferably, the substantially pure polypeptide (1) has an portion which is substantially identical, and preferably identical, to the amino acid sequence shown in SEQ ID NO:1, and (2) has the property of detectably inhibiting adhesion mediated by $\alpha_4\beta_1$ and/or of detectably inhibiting leukocyte adhesion, such as neutrophil adhesion to endothelium and/or transmigration of neutrophils across endothelium.

An embodiment of the present invention provides polynucleotides encoding polypeptides comprising a biologically active polypeptide segment of a tick-derived anti-inflammatory protein. Preferably, such a polynucleotide encodes a polypeptide having an amino terminal region which is substantially identical to the amino acid sequence shown in SEQ ID NO:1. More preferably, such polynucleotides comprise a nucleotide sequence shown in SEQ ID NO:2.

In one embodiment, the present invention also provides an expression vector comprising a polynucleotide sequence encoding a polypeptide comprising a biologically active polypeptide segment of a tick-derived anti-inflammatory protein, wherein said expression vector is capable of being expressed in a prokaryotic or eukaryotic cell. The invention also provides a cell containing said expression vector, and capable of expressing said polynucleotide sequence(s), and a method for culturing said cell to express such polypeptides. Frequently, a glycosylating cell will be used as an expression host if glycosylation is desired (e.g., for biological activity, stability, and the like).

In a further embodiment of the present invention is provided a pharmaceutical composition containing a protein comprising a biologically active polypeptide segment of a tick-derived anti-inflammatory protein, as well as methods of treating acute inflammatory diseases through the administration of an effective amount of said pharmaceutical composition.

The present invention also provides polyclonal and monoclonal antibodies which specifically bind to a tick-derived anti-inflammatory protein with a binding affinity of about at least $1 \times 10^7$ M$^{-1}$, preferably about at least $1 \times 10^8$ M$^{-1}$ or more, and a method of detecting a tick-derived anti-inflammatory protein in a target sample comprising the steps of contacting an antibody which specifically binds to a tick-derived anti-inflammatory protein with a target sample and measuring the formation of immunocomplexes.

In one embodiment of the invention, a tick anti-inflammatory polypeptide is provided as a commercial research reagent for various medical research and diagnostic uses. Such uses can include but are not limited to: (1) use as a calibration standard for quantitating inhibitory activities of candidate anti-inflammatory agents in neutrophil-to-endothelium adhesion and transmigration assays, (2) use to measure the capacity of neutrophils explanted from an individual patient to undergo endothelial adhesion and transmigration, thereby providing a diagnostic measurement of leukocyte (e.g., neutrophil) function and/or inflammation status, (3) use to inhibit neutrophil infiltration in explanted organs (e.g., liver, kidney, heart, etc.) or portions thereof maintained in organ culture, (4) other research and diagnostic applications wherein inhibition of leukocyte adhesion, leukocyte transmigration, or other integrin-mediated cell adhesion is preferably inhibited or such inhibition is conveniently calibrated against a known quantity of a tick-derived anti-inflammatory protein, and the like.

BRIEF DESCRIPTION OF THE FIGURES

FIG. 1 (SEQ. ID NO:1) shows an amino-terminal sequence of a 4 kD tick-derived anti-inflammatory protein isolated from tick salivary glands. Conventional three-letter amino acid code is used, with X signifying the presence of an unidentified amino acid. Parentheses indicate that the enclosed amino acid identification is uncertain.

DEFINITIONS

Figure 2:
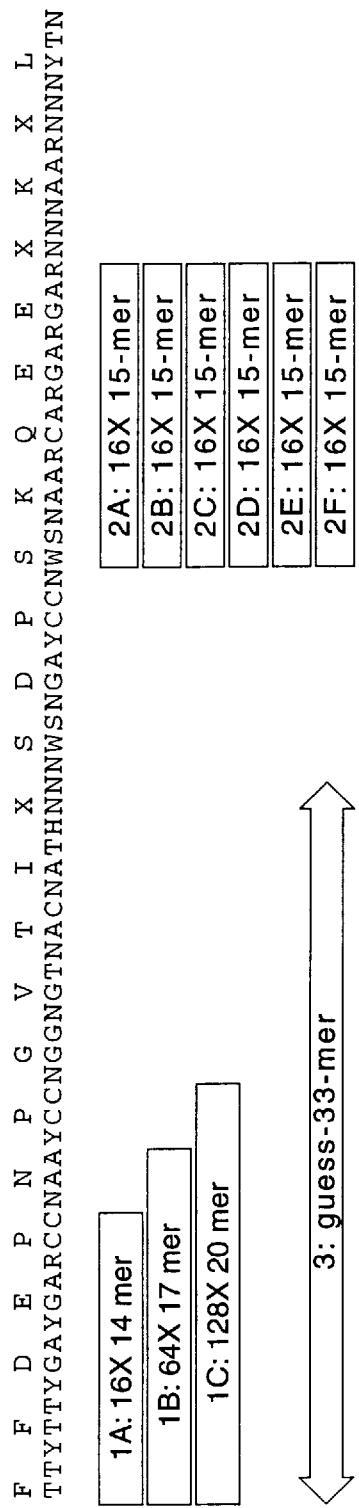
FIG. 2 (SEQ. ID NO:2) shows the amino-terminal sequence of a 4 kD tick-derived anti-inflammatory protein isolated from tick salivary glands using one-letter amino acid code (top), the degenerate polynucleotide sequence (middle), and example oligonucleotide probes 1A–1C, 2A–2F, and 3 (below). In reverse translating to polynucleotide sequence, in addition to the standard 4 DNA nucleotides: Y represents pyrimidine residues; R represents purine residues; N represents any nucleotide; W represents T or A; S represents C or G; H represents C, T, or A; and X represents unknown residue. Probes 1A, 1B, and 1C are derived from the reverse translation of the amino-terminus of the protein sequence, and represent a 16×, 64×, or 128× degenerate 14-mer, 17-mer, and 20-mer, respectively. Probe 1B is believed to be a preferred probe of the 1A–1C probes. Probes 2A–2F from Ser16-Glu22 represent 6 separate 16× degenerate oligonucleotides. Probe 3 is a 33-mer guessmer with inosine substitutions at the third position of degenerate codons according to the rules of Sambrook op.cit.

Unless defined otherwise, all technical and scientific terms used herein have the same meaning as commonly understood by one of ordinary skill in the art to which this invention belongs. A convenient reference for terminology is *Stedman's Medical Dictionary* 24th Ed., Williams and Wilkins, Baltimore). Although any methods and materials similar or equivalent to those described herein can be used in the practice or testing of the present invention, the preferred methods and materials are described. For purposes of the present invention, the following terms are defined below.

As used herein, the twenty conventional amino acids and their abbreviations follow conventional usage (*Immunology—A Synthesis*, 2nd Edition, E. S. Golub and D. R. Gren, Eds., Sinauer Associates, Sunderland, Mass. (1991), which is incorporated herein by reference). Stereoisomers (e.g., D-amino acids) of the twenty conventional amino acids, unnatural amino acids such as $\alpha,\alpha$-disubstituted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\omega$-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. Ticks cultured in the laboratory are considered naturally-occurring unless otherwise stated.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparision; a reference sequence may be a subset of a larger sequence, for example, as a segment of a full-length cDNA or gene sequence given in a sequence listing, such as a polynucleotide sequence of FIG. 2, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparision (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of a full-length tick-derived anti-inflammatory protein cDNA or a full-length tick-derived anti-inflammatory protein genomic gene.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

As used herein, the term "protein" refers to macromolecules which comprise one or more polypeptides wherein said polypeptides may comprise or lack post-translational modifications (e.g., glycosylation, cleavage, phosphorylation, side-chain derivation, and the like). For example, a 20 kD protein may comprise one or more polypeptides of less than 20 kD (e.g., 4 kD) and such polypeptides may comprise a post-translational modification (e.g., glycosylation).

As used herein, the term "tick-derived anti-inflammatory protein" refers to a protein having a sequence of at least 14 consecutive amino acids substantially identical to a protein encoded by an insect genome, such as a genome of a tick species, wherein the protein possesses a biological activity of inhibiting cell adhesion, for example leukocyte adhesion, such as neutrophil adhesion to endothelium and/or neutrophil transmigration across endothelium; and/or wherein the protein possesses an activity of inhibiting cell adhesion activity dependent upon one or more of the following adhesion molecule pairs: $\alpha_M\beta_2$(CD11b/CD18), $\alpha_L\beta_2$ (CD11a/CD18), $\alpha_5\beta_1$, $\alpha_4\beta_1$, and $\alpha_4\beta_7$.

As used herein, the term "biological activity" means the property of inhibiting cell adhesion, such as for example neutrophil adhesion to endothelium and/or neutrophil transmigration across endothelium; and/or wherein the protein possesses an activity of inhibiting adhesion dependent upon one or more of the following molecule pairs: $\alpha_M\beta_2$(CD11b/CD18), $\alpha_L\beta_2$(CD11a/CD18) $\alpha_5\beta_1$, $\alpha_4\beta_1$, $\alpha_4\beta_7$, and gpIIb/gpIIIa. Inhibition of cell adhesion involving non-leukocytic cells is also considered biological activity as used herein.

The term "native protein" as used herein refers to a polypeptide corresponding to a deduced amino acid sequence of a full-length cDNA or to a mature polypeptide present in a naturally-occurring tick-derived anti-inflammatory protein purified from ticks.

The term "fragment" as used herein refers to a polypeptide that has an amino-terminal and/or carboxy-terminal deletion, but where the remaining amino acid sequence is identical to the corresponding positions in the amino acid sequence of the naturally-occurring polypeptide(s) or deduced from a full-length cDNA sequence. Fragments typically are at least 14 amino acids long, preferably at least 20 amino acids long, usually at least 50 amino acids long or longer.

The term "analog" as used herein refers to polypeptides which are comprised of a segment of at least 14 amino acids that has substantial identity to a portion of a naturally-occurring tick-derived anti-inflammatory protein such as the 4 kD protein, and which has at least one of the following properties: (1) inhibits cell adhesion (e.g., adhesion of luekocytes to endothelium), (2) inhibits transmigration of neutrophils across endothelium and/or (3) inhibits adhesion dependent upon one or more of the following molecule pairs: $\alpha_M\beta_2$(CD11b/CD18), $\alpha_L\beta_2$(CD11a/CD18), $\alpha_5\beta_1$, $\alpha_4\beta_1$, $\alpha_4\beta_7$, and gpIIb/gpIIIa (e.g., see Experimental Examples, infra). Typically, analog polypeptides comprise a conservative amino acid substitution (or addition or deletion) with respect to the naturally-occurring sequence. Analogs typically are at least 20 amino acids long, preferably at least 50 amino acids long or longer, most usually being as long as full-length naturally-occurring tick-derived anti-inflammatory polypeptides. Some analogs may lack substantial biological activity but may still be employed for various uses, such as for raising antibodies to predetermined epitopes, as an immunological reagent to detect and/or purify reactive antibodies by affinity chromatography, or as a competitive or noncompetitive agonist, antagonist, or partial agonist of native tick-derived anti-inflammatory protein function.

The term "polypeptide" is used herein as a generic term to refer to native protein, fragments, or analogs of a tick-derived anti-inflammatory polypeptide. Hence, native protein, fragments, and analogs of a tick-derived anti-inflammatory protein are species of the tick-derived anti-inflammatory polypeptide genus.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

As used herein, "glycosylating cell" is a cell capable of glycosylating proteins, particularly eukaryotic cells capable of adding an N-linked "core oligosaccharide" containing at least one mannose residue and/or capable of adding an O-linked sugar, to at least one glycosylation site sequence in at least one polypeptide expressed in said cell, particularly a secreted protein. Thus, a glycosylating cell contains at least one enzymatic activity that catalyzes the attachment of a sugar residue to a glycosylating site sequence in a protein or polypeptide, and the cell actually glycosylates at least one expressed polypeptide. For example but not for limitation, mammalian cells are typically glycosylating cells. Other eukaryotic cells, such as insect cells and yeast, may be glycosylating cells.

DESCRIPTION OF THE PREFERRED EMBODIMENT

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document. The procedures therein are believed to be well known in the art and are provided for the convenience of the reader. All the information contained therein is incorporated herein by reference.

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. HA Erlich, Freeman Press, New York, N.Y. (1992); *PCR Protocols: A Guide to Methods and Applications*, eds. Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) *PCR Methods and Applications* 1: 17; *PCR*, eds. McPherson, Quirkes, and Taylor, IRL Press, Oxford; and U.S. Pat. No. 4,683,202, which are incorporated herein by reference).

A basis of the present invention is the finding that whole tick extracts, and more particularly tick salivary gland extracts, comprise a protein species which inhibits cell adhesion mediated by integrins and the like; and specifically the tick protein species inhibits leukocyte adhesion such as the binding of neutrophils to endothelium and/or transmigration of neutrophils across endothelial cells in culture. The protein species are termed "tick-derived anti-inflammatory proteins" and are present in salivary glands and related tissues of various tick genera and species (e.g., *Ixodes pacificus, Amblyomma americanum*), and can be present in other members of the phylum Arthropoda and particularly members of the class Insecta. The tick-derived anti-inflammatory protein species can be isolated from tick salivary gland by conventional biochemical purification methods. The tick-derived anti-inflammatory protein species generally possess the property(ies) of inhibiting leukocyte adhesion, such as neutrophil adhesion, and/or inhibiting neutrophil transmigration activity through a direct interaction with integrin molecules; typically, such proteins have higher inhibitory activity for $\alpha_5\beta_1$ and $\beta_2$ than for $\alpha_4\beta_1$, and substantially lack inhibitory activity towards members of the selectin and immunoglobulin families (e.g., $\alpha_1\beta_1$, $\alpha_3\beta_1$, $\alpha_6\beta_1$, VCAM-1, ICAM-1, P-selectin, E-selectin).

The tick-derived anti-inflammatory proteins and polypeptides of the invention can be used to treat or prevent pathological conditions dependent on leukocyte adhesion, such as neutrophil infiltration in inflammatory diseases, especially acute inflammatory diseases such as those characterized by acute ischemia and subsequent reperfusion injury (e.g., stroke, mechanical trauma, myocardial infarction, brain injury, spinal cord shock, and the like). Neutrophil infiltration occurring during or subsequent to an ischemic/reperfusion event is understood to induce tissue damage subsequent to the primary insult. Prevention or inhibition of such neutrophil infiltration will reduce the severity of secondary damage. The tick-derived anti-inflammatory proteins can also be used to treat other diseases in which cell adhesion (e.g., integrin-mediated cell adhesion) participates in the genesis or progression of the pathological condition; for example, cell adhesion is involved in invasion and metastatis of neoplastic cells in cancer, and may be involved in contol of the neoplastic phenotype.

The tick-derived anti-inflammatory proteins and polypeptides of the invention can be used to treat or prevent other types of leukocyte-mediated inflammatory diseases, such as those comprising $\alpha_4$-dependent lymphocytic infiltration (e.g., multiple sclerosis), and other neutrophil-mediated inflammatory diseases.

Pharmaceutical compositions comprising a therapeutically efficacious dose of a tick-derived anti-inflammatory protein and/or polypeptide can be administered to a human or veterinary patient to inhibit inflammation dependent upon leukocyte adhesion, especially mediated by neutrophil-infiltration. Frequently, such pharmaceutical compositions are administered by intravenous, intramuscular, or subcutaneous routes, although other routes may also be used depending upon the nature, location, and extent of the insult predisposing to the leukocyte adhesion-mediated disease or neutrophil-mediated inflammation.

The tick-derived anti-inflammatory proteins and polypeptides of the invention can be used as commercial reagents for a variety of diagnostic and research applications. For example, a composition comprising a predetermined concentration or activity of a tick-derived anti-inflammatory protein or polypeptide can be employed as a calibration standard for quantitating an activity of a candidate anti-inflammatory agent to inhibit neutrophil-endothelium adhesion and neutrophil transmigration, typically under in vitro endothelial cell culture conditions (e.g., such as an anti-inflammatory drug discovery screening system). Also for example, a composition comprising a predetermined concentration or activity of a tick-derived anti-inflammatory protein or polypeptide can be employed as a diagnostic reagent for determining the capacity of a leukocyte-containing explant from a patient to undergo cell adhesion (e.g., neutrophil-endothelial adhesion) and transmigration and/or for determining the capacity for such explanted leukocytes to exhibit integrin-dependent adhesion and transmigration inhibitable by a $\beta_2$ or $\alpha_4$ inhibitor (e.g., tick-derived anti-inflammatory protein). Such diagnostic measurements provide clinical information regarding a patient's leukocyte (e.g., neutrophil) activity, inflammatory condition status, and other clinical measures of immune system function.

I. Proteins, Polypeptides and Fragments

A. Characterization of Polypeptides

The tick-derived anti-inflammatory proteins and polypeptides of the present invention may be originally derived from the salivary glands of ticks or may be produced by expression of recombinant polynucleotides in host organisms or by direct chemical synthesis. In a specific embodiment of the present invention, the tick-derived anti-inflammatory protein is isolated from tick salivary glands and has an approximate molecular weight of 20 kD (hereafter "20 kD protein"). The tick-derived anti-inflammatory proteins of the present invention may alternatively be derived from tick salivary glands and have an approximate molecular weight of 4 kD (hereafter "4 kD protein"). The present invention also encompasses within its scope various complexes of the above described polypeptides, e.g., monomeric linear or cyclic forms, dimeric, trimeric, tetrameric, pentameric, or other oligomeric forms. Such complexes may be joined by disulfide bonds, hydrogen bonds, ether bonds, peptide bonds, or other known means of linking polypeptides.

In a specific embodiment, the polypeptides of the present invention may comprise a segment of about at least 14 contiguous amino acids, wherein the amino acid sequence of said segment is substantially identical, and preferably identical, to the amino acid sequence shown in SEQ ID NO:1. Typically, a segment having substantial homology to the amino acid sequence shown in SEQ ID NO:1 is present at or near the amino terminus of the polypeptide. Polypeptides possessing an amino-terminal amino acid sequence substantially homologous to the sequence shown in SEQ ID NO:1 will preferably be at least about 60–75% identical in the amino terminal region, to the sequence shown, more preferably, at least about 75–90% identical, and most preferably at least about 95% identical. This definition of amino-terminal sequence identity is intended to encompass polypeptides or fragments thereof, which substantially share primary structural sequence with that sequence shown in SEQ ID NO:1, as well as chemical and biochemical modifications/derivatives thereof (e.g., glycosylation, sulfation, phosphorylation, ubiquitination, disulfide bonds, and other minor alterations in the basic primary sequence including allelic variants and interspecies or intergeneric polymorphisms). These alterations may also include the binding of the polypeptides to a solid support. In some embodiments, these alterations may be useful as labelling reagents, or serve as purification targets, such as affinity ligands. Such embodiments will be readily appreciated by those skilled in the art.

The polypeptides of the present invention are provided in substantially pure form. The term "substantially pure" as used herein, describes polypeptide compositions wherein the polypeptides are separated from the native contaminants with which they are normally associated in their natural state. Typically, a polypeptide is substantially pure when it comprises about 60 to 90% w/w of the soluble matter in a sample, more preferably at least about 95%, and most preferably at least about 99%. The polypeptides of the present invention, when purified from the extract of tick salivary glands, synthesized in vitro, or expressed in a cellular system other than that which normally expresses said polypeptide, are separated from the native contaminants with which they are normally associated in their natural state, and thus are within the scope of the present invention.

The present invention also encompasses within its intended scope, biologically active fragments of the above described polypeptides. A biologically active fragment of these polypeptides are defined as a segment of amino acid residues of about at least 14 contiguous amino acids wherein the segment's amino acid sequence is substantially identical to a segment of the amino acid sequence of the tick-derived anti-inflammtory protein, and the fragment possesses the ability to inhibit leukocyte adhesion, and preferably neutrophil adhesion, to other cells or extracellular matrix (e.g., endothelial cells and basement membrane) and/or transmigration across endothelium.

Such fragments may be identified by chemical and or proteolytic digestion of polypeptides present in the 20 kD or 4 kD protein(s), and subsequent purification of the fragments using methods well known in the art, e.g., reverse phase liquid chromatography, affinity purification using known neutrophil surface receptors, and/or known endothelial receptors as affinity ligands, or other methods generally well known in the art. Purified fragments showing the ability to inhibit leukocyte adhesion or transmigration across endothelium can have their amino acid sequence determined utilizing methods well known in the art (e.g., Edman cycle degradation). Once identified and sequenced, such biologically active fragments may be produced by any of the above described methods, e.g., by chemical synthesis or using recombinant technology.

Fragments or analogs of tick-derived anti-inflammatory polypeptides (e.g., the 20 kD and 4 kD proteins) may be prepared by those of skill in the art. Preferred amino- and carboxy-termini of fragments or analogs occur near boundaries of functional domains. For example, but not for limitation, such functional domains include: (1) domains conferring the property of binding to an integrin and (2) domains conferring multimerization.

One method by which structural and functional domains may be identified is by comparison of the nucleotide and/or amino acid sequence data provided herein to public or proprietary sequence databases. Preferably, computerized comparison methods are used to identify sequence motifs or predicted protein conformation domains that occur in other proteins of known structure and/or function. For example, the NAD-binding domains of dehydrogenases, particularly lactate dehydrogenase and malate dehydrogenase, are similar in conformation and have amino acid sequences that are detectably homologous (*Proteins, Structures and Molecular Principles*, (1984) Creighton (ed.), W. H. Freeman and Company, New York, which is incorporated herein by reference). Further, a method to identify protein sequences that fold into a known three-dimensional structure are known (Bowie et al. (1991) *Science* 253: 164). Thus, the foregoing examples demonstrate that those of skill in the art can recognize sequence motifs and structural conformations that may be used to define structural and functional domains in the sequences of the invention.

Additionally, computerized comparison of sequences shown in FIGS. 1 or 2 to existing sequence databases can identify sequence motifs and structural conformations found in other proteins or coding sequences that indicate similar domains of the 4 kD protein. For example but not for limitation, the programs GAP, BESTFIT, FASTA, and TFASTA in the Wisconsin Genetics Software Package (Genetics Computer Group, 575 Science Dr., Madison, Wis.) can be used to identify sequences in databases, such as GenBank/EMBL, that have regions of homology with a tick-derived anti-inflammatory polypeptide sequence. Such homologous regions are candidate structural or functional domains. Alternatively, other algorithms are provided for identifying such domains from sequence data. Further, neural network methods, whether implemented in hardware or software, may be used to: (1) identify related protein sequences and nucleotide sequences, and (2) define structural or functional domains in polypeptides (Brunak et al. (1991) *J. Mol. Biol.* 220: 49, which is incorporated herein by reference).

Fragments or analogs comprising substantially one or more functional domain may be fused to heterologous polypeptide sequences, wherein the resultant fusion protein exhibits the functional property(ies) conferred by the fragment. Alternatively, polypeptides wherein one or more functional domain have been deleted will exhibit a loss of the property normally conferred by the missing fragment.

Although one class of preferred embodiments are fragments having amino- and/or carboxy-termini corresponding to amino acid positions near functional domains borders, alternative fragments may be prepared. The choice of the amino- and carboxy-termini of such fragments rests with the discretion of the practitioner and will be made based on experimental considerations such as ease of construction, stability to proteolysis, thermal stability, immunological reactivity, amino- or carboxyl-terminal residue modification, or other considerations.

In addition to fragments, analogs of tick-derived anti-inflammatory polypeptides can be made. Such analogs may include one or more deletions or additions of amino acid sequence, either at the amino- or carboxy-termini, or internally, or both or neither; analogs may further include sequence transpositions. Analogs may also comprise amino acid substitutions, preferably conservative substitutions. Additionally, analogs may include heterologous sequences generally linked at the amino- or carboxy-terminus, wherein the heterologous sequence(s) confer a functional property to the resultant analog which is not indigenous to the native tick-derived anti-inflammatory protein. However, analogs must comprise a segment of 14 amino acids that has substantial identity to a portion of the amino acid sequence of a naturally-occurring tick-derived anti-inflammatory polypeptide. Preferred amino acid substitutions are those which: (1) reduce susceptibility to proteolysis, (2) reduce susceptibility to oxidation, (3) alter post-translational modification of the analog, possibly including phosphorylation, sulfation, or glycosylation, and (4) confer or modify other physicochemical or functional properties of such analogs. Analogs include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside functional domains). Muteins and other analogs generally possess biological activity.

Conservative amino acid substitution is a substitution of an amino acid by a replacement amino acid which has similar characteristics (e.g., those with acidic properties: Asp and Glu). A conservative (or synonymous) amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles*, (1984) Creighton (ed.), W. H. Freeman and Company, New York; *Introduction to Protein Structure*, (1991), C. Branden and J. Tooze, Garland Publishing, New York, N.Y.; and Thornton et al. (1991) *Nature* 354: 105; which are incorporated herein by reference).

In addition to polypeptides consisting only of naturally-occuring amino acids, tick-derived anti-inflammatory peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15: 29; Veber and Freidinger (1985) *TINS* p.392; and Evans et al. (1987) *J. Med. Chem* 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as naturally-occurring tick-derived anti-inflammatory polypeptide, but have one or more peptide linkages optionally replaced by a linkage selected from the group consisting of: —$CH_2NH$—, —$CH_2S$—, —$CH_2$—$CH_2$—, —$CH$=$CH$—(cis and trans), —$COCH_2$—, —$CH(OH)CH_2$—, and —$CH_2SO$—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., *Trends Pharm Sci* (1980) pp. 463–468 (general review); Hudson, D. et al., *Int J Pept Prot Res* (1979) 14:177–185 (—$CH_2NH$—, $CH_2CH_2$—); Spatola, A. F. et al., *Life Sci* (1986) 38:1243–1249 (—$CH_2$—S); Hann, M. M., *J Chem Soc Perkin Trans I* (1982) 307–314 (—CH—CH—, cis and trans); Almquist, R. G. et al., *J Med Chem* (1980) 23:1392–1398 (—$OCH_2$—); Jennings-White, C. et al., *Tetrahedron Lett* (1982) 23:2533 (—$OCH_2$—); Szelke, M. et al., European Appln. EP 45665 (1982) CA: 97:39405 (1982) (—$CH(OH)CH_2$—); Holladay, M. W. et al., *Tetrahedron Lett* (1983) 24:4401–4404 (—$C(OH)CH_2$—); and Hruby, V. J., *Life Sci* (1982) 31:189–199 (—$CH_2$—S—); each of which is incorporated herein by reference. A particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., immunoglobulin superfamily molecules) to which the peptidomimetic binds to produce the therapeutic effect. Derivitization (e.g., labelling) of peptidomimetics should not substantially interfere with the desired biological or pharmacological activity of the peptidomimetic. Generally, peptidomimetics possess detectable biological activity, Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch (1992) *Ann. Rev. Biochem.* 61: 387, incorporated herein by reference); for example, by adding internal cysteine residues capable of forming intramolecular disulfide bridges which cyclize the peptide.

B. Methods of Producing the Polypeptides

1. Isolated From Salivary Glands of Ticks.

The polypeptides of the present invention may be extracted from whole tick extracts, salivary glands of ticks, or purified directly from the tick saliva. Some specific examples of ticks from which the polypeptides of the present invention can be derived are *Ixodes pacificus* and *Amblyomma americanum*, and the like. The polypeptides are purified from the extract or saliva using traditional purification methods known in the art. Specifically, the polypeptides may be purified using ion exchange chromatography, gel-filtration, reverse-phase liquid chromatography, or a stepwise combination thereof (see Example 1). To determine the effectiveness of a particular purification step, fractions are assayed for their ability to inhibit leukocyte adhesion and/or neutrophil transmigration across endothelial tissues (See Example 3(c)). Fractions showing such inhibitory activity are run on SDS-PAGE to determine approximate purity.

2. Chemical Synthesis or Recombinant Expression

Also within the intended scope of the present invention, are the above described polypeptides produced by chemical synthesis, or recombinant means. Techniques for chemical synthesis of peptides are generally well known in the art and are further described herein. Similarly, recombinant means for protein or polypeptide production are generally well known in the art and are further described below.

II. Polynucleotides

A. Identity

The polynucleotides of the present invention encompass polynucleotide seqeunces which encode polypeptides, derivatives, fragments, or analogs thereof, which are capable of inhibiting leukocyte (e.g., neutrophil) binding or transmigration across endothelial cells. Included within these polynucleotides are RNA, cDNA, genomic DNA, synthetic forms, and mixed polymers, both sense and antisense strands. The polynucleotides of this invention will generally be in the form of RNA or DNA, or mixed polymers thereof. The described DNA embodiment is usually derived from genomic DNA or cDNA prepared by synthesis.

The polynucleotides provided by the present invention can be readily used as probes, useful in obtaining substantially identical sequences, especially those encoding polypeptides of the present invention, from genomic cDNA libraries of other species. Similarly, the nucleotide sequence provided herein can be used to design oligonucleotide probes for screening such tick cDNA or genomic DNA libraries, or used as primers, e.g., for cloning substantially homologous sequences from other species, by means of a polymerase chain reaction (PCR) or other methods well known in the art. Portions of the DNA molecule having at least about 16 nucleotides, usually about 20 nucleotides, more usually about 30 nucleotides, and fewer than about 6 kilonucleotides (knt), and usually fewer than about 0.5 knt, are suitable probes. (Sambrook, et al., Molecular Cloning: A Laboratory Manual (2nd ed.), Vols. 1–3, Cold Spring Harbor Laboratory, (1989), and Current Protocols in Molecular Biology, F. Ausubel, et al., ed., Greene Publishing and Wiley Interscience, New York (1987 and periodic updates), for PCR, see, U.S. Pat. Nos. 4,683,195 and 4,683,202, PCR Technology, Erlich, ed., Stockton Press, New York (1989), and PCR Protocols: A Guide to Methods and Applications, Innis, et al., eds., Academic Press, San Diego (1990)).

In a particular embodiment, polynucleotides of the present invention encode the 20 kD polypeptide which is capable of inhibiting neutrophil adhesion or transmigration across endothelial tissue. Polynucleotides of the present invention can encode the 4 kD polypeptide which is capable of inhibiting neutrophil adhesion or transmigration across endothelial tissue. In a preferred embodiment, the polynucleotides encode a polypeptide having an N-terminal region wherein said region comprises an amino acid sequence which is substantially identical to that shown in SEQ ID NO:1. Specifically included within this embodiment are polynucleotide sequences, such as a mRNA obtained from tick salivary gland cells wherein the 5' region of said mRNA (or second-strand cDNA derived therefrom) contains a polynucleotide sequence which encodes substantially the N-terminal amino acid sequence shown in SEQ ID NO:1.

Genomic or cDNA clones encoding tick-derived anti-inflammatory polypeptides (e.g., the 4 kD protein or 20 kD protein) may be isolated from clone libraries (e.g., available from Clontech, Palo Alto, Calif.) using hybridization probes designed on the basis of the degenerate nucleotide sequences shown in FIG. 2 using conventional hybridization screening methods (e.g., Benton W D and Davis R W (1977) *Science* 196: 180; Goodspeed et al. (1989) *Gene* 76: 1). Where a cDNA clone is desired, clone libraries containing cDNA derived from tick salivary gland mRNA is preferred. Alternatively, synthetic polynucleotide sequences corresponding to all or part of the sequences shown in FIG. 2 may be constructed by chemical synthesis of oligonucleotides. Additionally, polymerase chain reaction (PCR) using primers based on the sequence data disclosed in FIG. 2 may be used to amplify DNA fragments from genomic DNA, mRNA pools, or from cDNA clone libraries. U.S. Pat. Nos. 4,683,195 and 4,683,202 describe the PCR method. Additionally, PCR methods employing one primer that is based on the sequence data disclosed in FIG. 2 and a second primer that is not based on that sequence data may be used. For example, a second primer that is homologous to or complementary to a polyadenylation segment may be used, as may random-sequence oligomers.

It is apparent to one of skill in the art that nucleotide substitutions, deletions, and additions may be incorporated into the polynucleotides of the invention. Nucleotide sequence variation may result from sequence polymorphisms of various alleles, minor sequencing errors, and the like. However, such nucleotide substitutions, deletions, and additions should not substantially disrupt the ability of the polynucleotide to hybridize to one of the polynucleotide sequences shown in FIG. 2 under hybridization conditions that are sufficiently stringent to result in specific hybridization.

Specific hybridization is defined herein as the formation of hybrids between a probe polynucleotide (e.g., a polynucleotide of the invention which may include substitutions, deletion, and/or additions) and a specific target polynucleotide (e.g., a polynucleotide having a sequence in FIG. 2), wherein the probe preferentially hybridizes to the specific target such that, for example, a single band corresponding to a tick-derived anti-inflammatory protein mRNA can be identified on a Northern blot of RNA prepared from a suitable cell source (e.g., a tick salivary gland). Polynucleotides of the invention and recombinantly produced polypeptides, and fragments or analogs thereof, may be prepared on the basis of the sequence data provided in FIG. 1 and FIG. 2 according to methods known in the art and described in Maniatis et al., *Molecular Cloning: A Laboratory Manual*, 2nd Ed., (1989), Cold Spring Harbor, N.Y. and Berger and Kimmel, *Methods in Enzymology*, Volume 152, *Guide to Molecular Cloning Techniques* (1987), Academic Press, Inc., San Diego, Calif., which are incorporated herein by reference.

Tick-derived anti-inflammatory polynucleotides may be short oligonucleotides (e.g., 25–100 bases long), such as for use as hybridization probes and PCR (or LCR) primers. Such polynucleotide sequences may also comprise part of a larger polynucleotide (e.g., a cloning vector comprising a cDNA clone) and may be fused, by polynucleotide linkage, in frame with another polynucleotide sequence encoding a different protein (e.g., glutathione S-transferase or β-galactosidase) for encoding expression of a fusion protein. Typically, such polynucleotides comprise at least 25 consecutive nucleotides which are substantially identical to a naturally-occurring tick-derived anti-inflammatory protein sequence (e.g., FIG. 1), more usually such polynucleotides comprise at least 50 to 100 consecutive nucleotides which are substantially identical to a naturally-occurring tick-derived anti-inflammatory protein gene sequence. However, it will be recognized by those of skill that the minimum length of a polynucleotide required for specific hybridization to a target sequence will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, polyamide nucleic acid, etc.), among others.

The invention also provides polynucleotides encoding the amino acid sequence shown in FIG. 1.

B. Method of Production

The polynucleotides of the present invention can be present in whole cells, cell lysates, or in partially purified or substantially pure form. An "isolated", substantially pure, or substantially homogenous polynucleotide is a polynucleotide which is substantially separated from other contaminants that naturally accompany it, e.g., protein, lipids, and other polynucleotide sequences. The term embraces polynucleotide sequences which have been removed or purified from their naturally-occurring environment, and include recombinant or cloned DNA isolates and chemically synthesized analogues or analogues biologically synthesized by heterologous systems.

An isolated polynucleotide will generally be a homogenous composition of molecules, but will, in some embodiments contain some heterogeneity. This heterogeneity is typically found at polymer ends or portions not critical to a desired biological function or activity. Purification of nucleic acid by standard techniques includes alkaline/sodium dodecyl sulfate (SDS) treatment, cesium chloride banding, column chromatography, and others well known in the art. (Current Protocols in Molecular Biology, F. Ausubel, et al., ed., Greene Publishing and Wiley Interscience, New York (1987)).

The polynucleotides of the present invention can be isolated and produced by methods generally well known in the art. Specifically, using the amino acid sequence for the desired protein or polypeptide (e.g., the amino acid sequence of FIG. 1), the polynucleotide can be isolated using reverse translation-based cloning with degenerate oligonucleotides encoding the predetermined amino acid sequence. Knowing the amino acid sequence of all or part of the desired polypeptide, regions of low degeneracy can be identified. Regions of low degeneracy comprise several amino acids wherein substantially all such amino acids have only a single possible codon which encodes for that amino acid, thus a nucleic acid which encodes such a region will have few or perhaps one possible nucleotide sequence. Because of the relatively small number of possible nucleotide sequences for these regions, only an equally small number of probes to these regions needs to be synthesized. Methods of chemically synthesizing oligonucleotide probes are generally well known in the art. This small number of probes is labelled and used to screen a tick genomic library or tick cDNA library (e.g., derived from whole ticks or tick salivary glands) to identify polynucleotides comprising a sequence which encodes the encoded polypeptide sequence.

Polynucleotides encoding a tick-derived anti-inflammatory protein may be isolated by PCR amplification of tick genomic DNA or reverse-transcriptase PCR amplification of tick mRNA; such amplification employs a primer or degenerate primer pool comprising a sequence of FIG. 2 and a second primer (e.g., a random sequence oligonucleotide).

Once isolated, the polynucleotide(s) can be incorporated into a suitable expression vector, which can be used to transform a suitable host cell which, in turn, can express the desired polypeptides. Such suitable expression vectors will generally comprise one or more DNA sequences encoding the polypeptides of the present invention, under the transcriptional control of a native or other promoter which is recognized by the host. Examples of suitable promoters include, e.g., the *E. coli* lac and trp promoters, the lambda $P^L$ and $P^R$ promoters, the yeast glycolytic enzyme promoters, the SV40 and adenovirus early and late promoters, and the like. Such constructs may further comprise transcription termination sequences, and sequences which encode leader or secretory signal sequences known in the art. Suitable vectors incorporating the above sequences will be capable of stable extrachromasomal maintenance in a suitable host or may be incorporated into the genome of the host.

Suitable host cells include a wide variety of procaryotic and eucaryotic organisms. Specific examples of suitable procaryotic hosts include *E. coli, Bacillus sp., Salmonella sp., Serratia marcescens*, and various Pseudomonas species. Specific eucaryotic hosts include yeasts, filamentous fungi, insect cells, mammalian cells, typically immortalized, e.g., various mouse cell lines, monkey cell lines, Chinese hamster ovary cell lines, human cell lines, derivatives of them, or the like. In some cases, the cells will be derived from a neoplastic host cell or wild-type cells will be transformed with oncogenes, oncogenic viruses or the like.

The above described expression vectors may be introduced into the host cell by any convenient means well known in the art. Such means include fusion, conjugation, transfection, transduction, electroporation, injection, lipofection, viral-based delivery, and the like.

III. Antibodies

A. Method of Preparation

The 20 kD polypeptide, the 4 kD polypeptide, or fragments or analogs thereof, will be useful for producing antibodies, either polyclonal or monoclonal, which possess specific binding for the respective polypeptides.

For production of polyclonal antibodies, an appropriate target immune system is selected, typically a mouse or rabbit. Other species may sometimes be substituted for a mouse or rabbit, including goats, sheep, cows, guinea pigs, and rats. Substantially purified 20 kD or 4 kD polypeptide or a fragment or analog thereof, is presented to the immune system in a fashion determined by methods appropriate for the animal and other parameters well known to those of ordinary skill in the art. Typical sites for injection are in the footpads, intramuscularly, intraperitoneally, or intradermally. The immunoglobulins produced by the host can be precipitated, isolated, and purified, including affinity purification.

For monoclonal antibodies, appropriate animals will be selected and the desired immunization protocol followed. After the appropriate period of time, the spleens of such animals are excised and individual spleen cells fused, typically, to immortalized myeloma cells under appropriate selection conditions. Thereafter the cells are clonally separated and the supernatants of each clone are tested for their production of an appropriate antibody specific for the desired region of the antigen. Techniques for producing antibodies are well known in the literature, see, e.g., Goding, et al., Monoclonal Antibodies: Principles and Practice (2d ed.) Academic Press, N.Y., and Harlow and Lane Antibodies: A Laboratory Manual, Cold Spring Harbor Laboratory, New York (1988), and are exemplified by U.S. Pat. Nos. 4,381,292, 4,451,570 and 4,618,577). Other suitable techniques involve in vitro exposure of lymphocytes to the antigenic polypeptides or alternatively to selection of libraries of antibodies in phage or similar vectors. (Huse, et al., "Generation of a Large Combinatorial Library of the Immunoglobulin Repertoire in Phage Lambda," Science 246:1275–1281 (1989)). Monoclonal antibodies with affinities of $10^8$ liters/mole, preferably $10^9$ to $10^{10}$ or stronger, will typically be made by these standard procedures.

Native tick-derived anti-inflammatory proteins, fragments thereof, or analogs thereof, may be used to immunize an animal for the production of specific antibodies. These antibodies may comprise a polyclonal antiserum or may comprise a monoclonal antibody produced by hybridoma cells. For general methods to prepare antibodies, see Antibodies: A Laboratory Manual, (1988) E. Harlow and D. Lane, Cold Spring Harbor Laboratory, Cold Spring Harbor, N.Y., which is incorporated herein by reference.

For example but not for limitation, a recombinantly produced fragment of the 4 kD protein can be injected into a mouse along with an adjuvant following immunization protocols known to those of skill in the art so as to generate an immune response. Typically, approximately at least 1–50 μg of a fragment or analog is used for the initial immunization, depending upon the length of the polypeptide. Alternatively or in combination with a recombinantly produced polypeptide, a chemically synthesized peptide having a 4 kD sequence (e.g., peptides having the sequence of FIG. 1) may be used as an immunogen to raise antibodies which bind a the naturally-occurring tick protein, such as the native 4 kD polypeptide comprising the sequence shown essentially in FIG. 1. Immunoglobulins which bind the recombinant fragment with a binding affinity of at least $1 \times 10^7$ $M^{-1}$ can be harvested from the immunized animal as an antiserum, and may be further purified by immunoaffinity chromatography or other means. Additionally, spleen cells are harvested from the immunized animal (typically rat or mouse) and fused to myeloma cells to produce a bank of antibody-secreting hybridoma cells. The bank of hybridomas can be screened for clones that secrete immunoglobulins which bind the recombinantly produced polypeptide (or chemically synthesized polypeptide) with an affinity of at least $1 \times 10^6$ $M^{-1}$. Animals other than mice and rats may be used to raise antibodies; for example, goats, rabbits, sheep, and chickens may also be employed to raise antibodies reactive with a protein. Transgenic mice having the capacity to produce substantially human antibodies also may be immunized and used for a source of antiserum and/or for making monoclonal-secreting hybridomas.

Bacteriophage antibody display libraries may also be screened for binding to a tick-derived anti-inflammatory polypeptide, such as a full-length protein, a fragment or analog, or a fusion protein comprising a polypeptide sequence of at least 14 contiguous amino acids of a tick-derived anti-inflammatory protein (e.g., as shown in FIG. 1). Combinatorial libraries of antibodies have been generated in bacteriophage lambda expression systems which may be screened as bacteriophage plaques or as colonies of lysogens (Huse et al. (1989) Science 246: 1275; Caton and Koprowski (1990) Proc. Natl. Acad. Sci. (U.S.A.) 87: 6450; Mullinax et al (1990) Proc. Natl. Acad. Sci. (U.S.A.) 87: 8095; Persson et al. (1991) Proc. Natl. Acad. Sci. (U.S.A.) 88: 2432). Various embodiments of bacteriophage antibody display libraries and lambda phage expression libraries have been described (Kang et al. (1991) Proc. Natl. Acad. Sci. (U.S.A.) 88: 4363; Clackson et al. (1991) Nature 352: 624; McCafferty et al. (1990) Nature 348: 552; Burton et al. (1991) Proc. Natl. Acad. Sci. (U.S.A.) 88: 10134; Hoogenboom et al. (1991) Nucleic Acids Res. 19: 4133; Chang et al. (1991) J. Immunol. 147: 3610; Breitling et al. (1991) Gene 104: 147; Marks et al. (1991) J. Mol. Biol. 222: 581; Barbas et al. (1992) Proc. Natl. Acad. Sci. (U.S.A.) 89: 4457; Hawkins and Winter (1992) J. Immunol. 22: 867; Marks et al. (1992) Biotechnology 10: 779; Marks et al. (1992) J. Biol. Chem. 267: 16007; Lowman et al (1991) Biochemistry 30: 10832; Lerner et al. (1992) Science 258: 1313, incorporated herein by reference). Typically, a bacteriophage antibody display library is screened with a tick-derived anti-inflammatory polypeptide that is immobilized (e.g., by covalent linkage to a chromatography resin to enrich for reactive phage by affinity chromatography) and/or labeled (e.g., to screen plaque or colony lifts).

Tick-derived anti-inflammatory polypeptides which are useful as immunogens or for screening a bacteriophage antibody display library are suitably obtained in substantially pure form, that is, typically about 50 percent (w/w) or more purity, substantially free of interfering proteins and contaminants. Preferably, these polypeptides are isolated or synthesized in a purity of at least 80 percent (w/w) and, more preferably, in at least about 95 percent (w/w) purity, being substantially free of other proteins of humans, mice, or other contaminants.

For some applications of these antibodies, such as identifying immunocrossreactive proteins, the desired antiserum or monoclonal antibody(ies) is/are not monospecific. In these instances, it may be preferable to use a synthetic or recombinant fragment of a tick-derived anti-inflammatory polypeptide as an antigen rather than using the entire native protein. More specifically, where the object is to identify immunocrossreactive polypeptides that comprise a particular structural moiety, such as a integrin-binding domain, it is preferable to use as an antigen a fragment corresponding to part or all of a commensurate structural domain in the tick-derived anti-inflammatory protein.

Such sequences as shown in FIG. 1 may be used as an immunogenic peptide directly (e.g., to screen bacteriophage antibody display libraries or to immunize a rabbit), or may be conjugated to a carrier macromolecule (e.g., BSA) or may compose part of a fusion protein to be used as an immunogen. If an antiserum is raised to a fusion polypeptide, such as a fusion protein comprising a tick-derived anti-inflammatory protein immunogenic epitope fused to $\beta$-galactosidase or glutathione S-transferase, the antiserum is preferably preadsorbed with the fusion partner (e.g, $\beta$-galactosidase or glutathione S-transferase) to deplete the antiserum of antibodies that react (i.e., specifically bind to) the non-Lyar portion of the fusion protein that serves as the immunogen.

B. Methods of Use

The above described antibodies can be useful in detecting the presence of the polypeptides of the present invention by contacting the antibodies with a sample containing the polypeptides, and detecting the amount of immunocrossreactivity. Such detection can be useful in determining dosage requirements of a patient to whom the compositions of the present invention have been administered. Methods of detecting and quantifying such crossreactivity are generally well known in the art. See, e.g., Goding, Monoclonal Antibodies: Principles and Practice (2d ed.) Academic Press, New York (1986).

One use of such antibodies is to screen cDNA expression libraries, preferably containing cDNA derived from tick mRNA from various tissues (e.g., whole ticks or salivary glands), for identifying clones containing cDNA inserts which encode structurally-related, immunocrossreactive proteins, that are candidate novel tick-derived anti-inflammatory proteins. Such screening of cDNA expression libraries is well known in the art, and is further described in Young et al. (1983) *Proc. Natl. Acad. Sci. U.S.A.* 80: 1194, which is incorporated herein by reference] as well as other published sources. Another use of such antibodies is to identify and/or purify immunocrossreactive proteins that are structurally or evolutionarily related to the native tick-derived anti-inflammatory protein or to the corresponding fragment (e.g., functional domain; DNA-binding domain) used to generate the antibody. Libraries of polynucleotide sequences derived from other (i.e., non-tick) animal species may be employed, preferably insects (e.g., mosquitos, biting flies, etc.).

IV. Methods of Using the Polypeptides of the Present Invention, and Compositions Incorporating Said Polypeptides The polypeptides of the present invention demonstrate the ability to inhibit adhesion which is dependent on a number of molecules within the integrin family (See Example 3, generally). Specifically, samples containing the polypeptides of the present invention have been found to inhibit $\alpha M\beta 2$ (CD11b/CD18), $\alpha L\beta 2$ (CD11a/CD18), $\alpha 5\beta 1$, $\alpha 4\beta 1$, and $\alpha 4\beta 7$ dependent adhesion (See examples below). This inhibitory activity has been discovered to result not through a nonspecific mechanism, but rather through direct interaction with the integrin molecule (See Example 3—Cell Free Assay).

A. Method of Use

1. Inhibition of $\beta 2$-Dependent Interaction

Neutrophil infiltration and accumulation has been shown to be mediated by, or dependent on the $\beta 2$-integrin subunit. See, for example, Tuonamen, et al., and Tanaka, et al., supra, where in vivo administration of antibodies to the $\beta 2$-subunit of CD18 markedly inhibited neutrophil binding and accumulation in central nervous system endothelial tissue and coronary endothelial tissue, respectively. As an inhibitor of $\beta 2$-dependent interaction (see Example 3(a) and (b)), the peptides of the present invention are particularly useful in preventing neutrophil infiltration and accumulation in an acute inflammatory response. Specific instances where such inhibition is desired include stroke or other cerebral trauma, where neutrophil infiltration occurring during ischemia and reperfusion is believed to induce damage in the tissue surrounding the primary injury.

Additionally, such inhibition may be particularly useful in preventing neutrophil infiltration and accumulation in patients suffering from antigen arthritis, or the reverse passive Arthus reaction.

2. Inhibition of $\alpha 4$-Dependent Interaction

The ability of compositions of the present invention to inhibit $\alpha 4$-dependent interactions is also a particularly useful aspect of the present invention (See Example 3(c)). Leukocyte penetration of the blood-brain barrier in multiple sclerosis (MS) is known to result in damage to myelin, further resulting in impaired nerve conduction and paralysis. Paterson, P. Y., in Textbook of Immunopathology, 179–213, Mischler and Mueller-Eberhard, eds., Grune and Stratton, New York (1986). Antibodies to $\alpha 4\beta 1$ integrin, were shown to inhibit binding of monocytes and lymphocytes to inflamed brain vessels with experimental autoimmune encephalomyelitis (EAE), a model condition similar to MS. Yednock, T. A., et al., Nature 356:63–66 (1992), See, also, Experimental Allergic Encephalomyelitis: A Useful Model for Multiple Sclerosis, 1–511, Alvord, E. C. (ed.), Liss, N. Y. (1984). Further, when tested in vivo, administration of these antibodies prevented the infiltration and accumulation of leukocytes in the central nervous system, and the development of EAE.

3. Compositions Containing the Compounds of the Present Invention

The compositions of the present invention, having the ability to inhibit $\alpha 4$ dependent interactions, can thus be particularly useful in an application similar to that described in Yednock, et al. Furthermore, these compositions may avoid the antigenic responses generally associated with the administration of non-human antibodies.

Effective doses of the compositions of the present invention, for the treatment of the above described conditions will vary depending upon many different factors, including means of administration, target site, physiological state of the patient, and other medicants administered. Thus treatment dosages will need to be titrated to optimize safety and efficacy. These compositions may be administered to mammals for veterinary use and for clinical use in humans in a manner similar to other therapeutic agents, i.e, in a physiologically acceptable carrier. In general, the administration dosage will range from about 0.0001 to 100 mg/kg, and more usually 0.001 to 0.1 mg/kg of the host body weight. Various considerations are described, e.g., in Gilman et al. (eds) Goodman and Gilman's: The Pharmacological Bases of Therapeutics, 8th Ed., Pergamon Press (1990); and Remington's Pharmaceutical Sciences, 17th ed., Mack Publishing Co., Easton, Pa. (1990)). Pharmaceutically acceptable carriers or diluents will include water, saline, buffers, and other compounds described, e.g., in the Merck Index, Merck & Co., Rahway, N.J. Slow release formulations, or slow release apparatus will often be utilized for continuous administration.

The pharmaceutical compositions will be administered by parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules, and lozenges.

The pharmaceutical compositions will often be administered intravenously. Thus, this invention provides compositions for intravenous administration which comprise a solution of the compound dissolved or suspended in an acceptable carrier, preferably an aqueous carrier. A variety of aqueous carriers can be used, e.g., water, buffered water, 0.4% saline, and the like. These compositions will sometimes be sterilized by conventional, well known sterilization techniques, or can be sterile filtered. The resulting aqueous solutions can be packaged for use as is, or lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 1–95% of active ingredient, preferably about 20%.

For aerosol administration, the compounds are preferably supplied in finely divided form along with a surfactant and propellant. The surfactant should, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Often mixed esters, such as mixed or natural glycerides will be employed. The surfactant, in some embodiments, will constitute 0.1%–20% by weight of the composition, preferably 0.25–5%. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above will sometimes also be employed. In producing the aerosol, a container equipped with a suitable valve is filled with the appropriate propellant, containing the finely divided compounds and surfactant. The ingredients are thus maintained at an elevated pressure until released by action of the valve.

The compositions containing the compounds can be administered for prophylactic and/or therapeutic treatments. In therapeutic applications, compositions are administered to a patient suspected of, or already suffering from, a disease, as described above, in an amount sufficient to cure, or at least partially arrest, the symptoms of the disease and its complications. An amount adequate to accomplish this is defined as "therapeutically-or pharmaceutically-effective dose." Amounts effective for this use will depend on the severity of the disease and the weight and general state of the patient.

In prophylactic applications, compositions containing the protein of the invention are administered to a patient susceptible to, or otherwise at risk of, a particular disease. Such an amount is defined to be a "prophylactically effective dose." In this use, the precise amounts again depend on the patient's state of health and other parameters.

4. Compounds of the Present Invention as Affinity Targets for Integrin Binding

The polypeptides of the present invention have been shown to exhibit a binding affinity for integrin molecules (See Example 3(f)). The skilled artisan would thus recognize that the polypeptides of the present invention, exhibiting such binding affinity, would be particularly useful as affinity ligands. Such ligands are particularly useful in the selective binding and or purification of integrin from solutions containing same. Methods of using these ligands in this manner are generally well known in the art. Specifically, such ligands may be bound to a solid support, e.g., activated sepharose, or the like, for use as an affinity resin in the purification of integrin.

Samples containing integrin are contacted with the ligand under conditions which permit specific binding. Such conditions are generally known in the art or can be determined by routine experimentation. The bound integrin is washed to eliminate other contaminants in the sample which are not specifically bound to the ligand. The integrin can then be eluted from the affinity resin. Such elution may be accomplished by a change in the pH or salt concentration of the washing buffer, and ideal conditions would be a matter of routine experimentation to one skilled in the art.

EXAMPLES

The present invention is illustrated further using the following examples. These examples are not intended to limit the scope of the invention.

Example 1
Purification of Proteins or Peptides.

Tick salivary glands at a concentration of 339 glands/mL were extracted, using first a 45% $(NH_4)_2SO_4$ cut followed by an 80% cut. The resulting pellet was resuspended in 1.7 mL PBS/0.2 mM EDTA which resulted in approximately a 2-fold concentration.

This solution was applied to a gel filtration column ("BIO-SIL", SEC-250, 7.5 mm×600 mm, Bio-Rad, Richmond, Calif.) in PBS containing EDTA and fractions showing the ability to inhibit leukocyte binding as determined by in vitro assay using cultured brain endothelial cells were pooled. Fractions resulting from the various purification steps were assayed for the ability to inhibit $\alpha 4\beta 1$-dependent interaction (See Example 3(c)). The activity eluted from the gel filtration column in 2 separate peaks, and the fractions corresponding to these peaks were pooled separately (fractions (F)19–21, and F24,25), and subject to independent purification. Based upon the elution profile from the gel filtration column, the molecular weights of the respective inhibiting polypeptides was determined to be approximately 20 kD for fractions 19–21, and 4 kD for fractions 24,25.

The respective pools were run independently on "MONO-Q" (Pharmacia, Piscataway, N.J.) anion exchange columns at pH 8.5, washed with starting buffer (20 mM Tris, pH 8.5, 0.2 mM EDTA), and eluted with a NaCl gradient. The elution profile of above fractions 19–21, again showed two separate peaks of activity (F7, pool 1, and F13–15, pool 2), while the above F24,25 pool resulted in a single activity peak from the "MONO-Q" elution (F13,F14, pool-3).

Each of pools 1, 2 and 3 were then further purified using reverse phase liquid chromatography (RPLC) on a Vydac C-4 column, 2.1×150 mm with a solvent system of 0.1% TFA in acetonitrile, and consecutively eluted fractions showing activity were pooled. (F22–24, F26–27 from pool 1; F26–32 from pool 2; F29,30 from pool 3).

Analysis of F29 and 30 from pool 3, using diode array spectrophotometry showed that these fractions appeared to contain substantially only one component. Additionally, from the RPLC elution profile of pools 1 and 2 respectively, the fractions from these runs were also determined to be substantially pure.

Example 2
Characterization of Protein or Peptides- N-Terminal Sequencing

Pooled fractions F29 and 30 from pool 3 above were analyzed for amino acid composition, which confirmed the molecular weight of the polypeptide as 4 kD with an estimated length of approximately 40 amino acids. The pool was also analyzed for N-terminal amino acid sequence determination. The first 20 amino acids of the N-terminal sequence of this polypeptide are shown in SEQ ID NO:1.

Example 3
Activity Determination

The polypeptides of the present invention, and purification samples thereof, were assayed for their ability to inhibit certain interactions which are dependent upon various members of the family of integrin molecules.

a. Neutroohil Transmigration Assay (A β2-Dependent Interaction).

Samples (extracts) containing the polypeptides of the present invention were assayed for their ability to inhibit neutrophil transmigration across endothelial tissues using the following methods.

Microvascular endothelial cells were isolated from either bovine (BBEC) or rat (RBEC) brain according to methods known in the art. RBEC were plated on collagen type-I coated filters (Transwell 3μm pore size, Costar). The filters were then placed in a 24-well cluster plate (Corning). Confluency of the monolayer was tested by rhodamine phalloidin staining.

Human neutrophil were isolated from healthy human donors. Blood was collected in EDTA, loaded onto polymorphprep medium (Gibco), and spun 30 minutes at 400 g. The plasma and the mononuclear cells band were discarded, and the neutrophil band collected. The neutrophils were washed with RMPI/10 mM EDTA, labeled with a fluorescent marker (Zynaxis, PA), and washed twice with RPMI/5% FBS/10 mM EDTA. After the last wash, cells were resuspended in RPMI/5% FBS at a cell density of $2\times10^6$/mL.

The RBEC were stimulated with TNF (tumor necrosis factor) for 4 hours, and washed once with the assay medium (RPMI/5% FBS) prior to the assay. The medium was aspirated, and 600 μL of assay medium with chemoattractant (100 nM fMLP or 10 nM IL-8) was added in the cluster plate, below the filter. 100 μL of cells was added onto the filter, and the sample to be tested was added to the cells at that time. Transmigration was allowed take place for 30 minutes at 37° C.

The filters were washed twice with PBS to remove unbound neutrophils. The medium below was collected, spun in a microfuge, and resuspended in 40 μL of 0.1% Triton, to extract the fluorescent dye. Fluorescence was read on an automated fluorimeter (Pandex).

Whole tick salivary gland extracts exhibited strong inhibition of neutrophil transmigration across both Rat Brain and Bovine Brain endothelial cells. Specifically, various samples of extracts yielded from about 63% to 100% inhibition of neutrophil transmigration, with most smples falling between 80% and 100% inhibition.

b. Neutrophil Binding Assay

To specifically assay for inhibition of neutrophil binding, the following method was used.

RBEC were plated onto 96-well plates (Corning) coated with collagen. Human neutrophils were isolated and labelled as described above. Neutrophils were either preincubated with the sample to be assayed for 30 minutes on ice, or the extract was added at the time of the assay. RBEC were TNF stimulated for either 4 or 24 hours, and washed as described above. 100 μL of cells at a density of $2\times10^6$ was added to the wells. Binding was allowed to take place for 30 minutes at room temperature. The plates were then washed four times and the cells were extracted and measured in the fluorimeter as described above.

Both tick saliva and tick salivary gland extract markedly inhibited neutrophil adhesion to RBEC. Salivary gland extract described above, diluted 1:300 showed substantially complete inhibition of neutrophil adhesion to TNF-stimulated RBEC, and approximately a 3-fold reduction in adhesion to nonstimulated RBEC.

c. U937 Binding Assay (An α4β1 Dependent Interaction).

The polypeptides of the present invention were also assayed for their ability to inhibit U937 leukocyte (monocytic cell line available from ATCC, Rockville, Md.; Tananka et al. (1989) Cell. Immunol. 122: 96) binding to RBEC, an α4β1-dependent interaction, using substantially the same method described for assaying neutrophil binding to RBEC. U937 cells however, were used at a density of only $10^6$/mL.

Tick salivary gland extracts substantially inhibited adhesion of U937 leukocytes to RBEC, resulting in a greater than 95% inhibition.

Samples containing the polypeptides of the invention were similarly assayed for their ability to inhibit U937 binding to VCAM-1 (vascular cell adhesion molecule), also an α4β1 dependent interaction, or fibronectin, an α4β1, α5β1 dependent interaction.

For this assay, RIA/EIA plates (Costar) were coated overnight at 4° C. with either 200 ng/mL of VCAM-1 (purified from human VCAM-1 transfected L-cells) or 10 μg/mL of fibronectin (Telios). Plates were blocked with 1% BSA in PBS with $Ca^{2+}/Mg^{2+}$ at 4° C. for 1–3 hours, and then washed 3 times with PBS. Binding was measured using the methods described above.

Binding of U937 cells to VCAM was completely inhibited in the presence of salivary gland extract, but was not inhibited if the extract-containing medium was washed out.

However, inhibition of U937 binding to fibronectin remained complete even after two washings. This indicates a stronger affinity for α5β1 involved in fibronectin binding, than for α4β1 involved in VCAM binding.

d. 8866 Aggregation (αLβ2-Dependent Interaction) and VCAM Binding (α4β7-Dependent Interaction)

Samples containing the polypeptides of the present invention were assayed for their ability to inhibit αLβ2-dependent interactions by determining their ability to inhibit aggregation of 8866 cells, a β2 dependent interaction. 8866 cells (Bujanowski-Weber et al. (1989) *Immunoloay* 66: 505; available from ATCC, Rockville, Md.) spontaneously aggregate. 200 μL of resuspended 8866 cells were incubated in a 96-well plate at 37° C. for 90 minutes, 5 hours, and 24 hours in the presence of samples containing the polypeptides of the present invention. The amount of aggregation for each time point was rated visually.

8866 Binding to RBEC.

Treatment of 8866 cells showed a perceivable inhibition of cell aggregation.

Similarly, the polypeptides of the present invention were tested for their ability to inhibit α4β7-dependent interactions by assaying their effect on binding of 8866 cells to VCAM. This assay was performed substantially as described for the U937 binding to VCAM.

e. Platelet Aggregation Assay (gpIIbIIIa-Dependent Interaction).

Platelet rich plasma (PRP) was obtained by spinning ACD collected human blood for 10 minutes at 400 g. 100 μL of PRP was pre-incubated 20 minutes at room temperature with either an antibody against gpIIb/IIIa, a serial dilution of a sample to be tested, or a control buffer. Aggregation was induced by addition of ADP at 20 μM final concentration. The platelets were then incubated at 37° C. with gentle mixing. The level of aggregation was detected using the change in light scatter distribution using the FACS.

Whole tick salivary gland extracts exhibited a dose dependent inhibition of platelet aggregation in comparison to the buffer control.

f. Cell Free Assay (Soluble α4β1 and α5β1 binding to Fibronectin)

Compositions containing the polypeptides of the present invention were tested for their ability to bind to integrin. The assay was based upon a comparison of integrin binding to fibronectin, an α4β1 and α5β1 dependent interaction, wherein either the integrin or the fibronectin was preincubated with compositions of the present invention. The method is set forth below:

U937 leukocyte cells were incubated with TS2/16, an antibody which activates β1 integrin, and Mn2+ to enhance the activation state of α4β1 and α5β1, at 4° C. for 30 minutes. Cells were washed with HEPES/saline/0.5% BSA, without $Ca^{2+}$ or $Mg^{2+}$, to remove unbound TS2/16 antibody and with 0.2 mM EDTA to remove serum fibronectin. The cells were lysed in 1% Triton with 1 mM $Mn^{2+}$ for 1 hour at 4° C. at a cell density of $2.6×10^7$/mL. The lysate was then preincubated with anti-α4/α5 antibodies, a composition of polypeptides of the present invention, or a buffer control, at 4° C. for 30 minutes. 50 μL of the treated lysates were then added to human fibronectin (FN) coated wells blocked with BSA, in multiwell plates. Similar plates were prepared wherein untreated lysates were added to the fibronectin coated wells, where the wells were preincubated with the antibodies, polypeptides, or control buffer, and washed to remove unbound material. The binding reaction in each instance, proceeded for 30 minutes at room temperature. The plates/wells were washed 3 times, and 100 μL of 1:1000 Gam-HRP (Horseradish Peroxidase) was added to each well and allowed to sit for 30 minutes at room temperature. Gam-HRP recognizes and binds to TS2/16 antibody which serves as a tag. The plates/wells were washed 4 times to remove unbound Gam-HRP. The wells were then developed using OPD (o-phenyldiamine) in the presence of hydrogen peroxide. The level of integrin binding to fibronectin was measured spectrophotometrically, and compared as a percentage of control binding (No inhibitor of integrin-fibronectin interaction=100%).

When the preincubated with the cell lysate, the salivary gland extract prevented binding of solubilized integrin to the fibronectin, whereas the buffer control did not. No inhibition of integrin binding to fibronectin was seen where the fibronectin plates/wells were preincubated with salivary gland extract, and washed. This indicates that the salivary gland extract acts directly on the integrin.

Example 4

Cloning of the Genes Encoding the Polypeptides of the Present Invention (Strategy).

The N-terminal amino acid sequence of the present polypeptide was determined for 20 residues, and this is shown in SEQ ID NO:1. Based upon this amino acid sequence, a degenerate nucleotide sequence can be predicted, using known amino acid/codon conversions. Additionally, from the amino acid sequence, regions of relative low degeneracy can be identified, e.g., regions within the amino acid sequence where substantially all of the individual amino acids have but a single codon which encodes therefor. Two such regions have been identified using the present amino acid sequence, aa 16-20 (corresponding nucleotides 46–60), and the N-terminal region of the polypeptide. All amino acid residues within the 16-20 region are encoded by single codons, except for the Ser residue at position 16, which may be encoded by 6 separate codons. Similarly, the stretch of 17 nucleotides at the N-terminus was determined to be the optimal compromise between length and degeneracy for later use as a probe.

6 probes are to be synthesized to correspond to the degenerate nucleotide sequence of the residue 16-20 region, each incorporating a separate codon for the Ser residue. Each of the 6 probes will be assessed individually by hybridization, to determine which probe matches the Ser codon used in the cDNA of the tick salivary gland. Additionally, a 17mer oligonucleotide probe corresponding to the 5' (N-terminal) nucleotide sequence is to be synthesized.

A tick salivary gland cDNA library was constructed in a bacteriophage λ vector (λZAPII, Stratagene Inc., La Jolla, Calif.) as well as a plasmid vector for mammalian cell expression (pcDNA3, Invitrogen Corp., San Diego, Calif.) using standard methods known in the art. See, e.g., Sambrook et al., in Molecular Cloning: A Laboratory Manual (2d ed.), 11.1–16, Cold Spring Harbor Laboratory, New York (1989) and Berger, et al., in Methods in Enzymology 152: Guide to Molecular Cloning Techniques, Section VIII, Academic Press, New York (1987). These vectors both have phage RNA polymerase promoters flanking the cDNA insert cloning sites which allows in vitro transcription of RNA from the cDNA inserts in the library.

The degenerate oligonucleotide probes described above are used to probe in vitro transcribed RNA from the cDNA library, by Northern Blot analysis, to confirm the presence of complementary sequences in the library, as well as validate the hybridization conditions to be used in screening the actual library. These probes will also be used as primers for PCR amplification of target sequences in order to obtain a defined, non-degenerate, nucleic acid probe for library screening purposes.

Suitable complementary sequences are obtained using the 2 methods described above (either the probes, or their amplified counterparts), as evidenced by hybridization with well defined bands. These probes are then used to screen the cDNA library. Alternatively, where these two methods fail to identify suitable complementary sequences, a new library may be constructed using a different batch of polyA⁺ mRNA from tick salivary glands, and this new library will be appropriately evaluated as above.

Screening of the library involves a dual probe approach. Specifically, the 5' 17 mer (probe 1) and the appropriate probe from the residue 16-20 region (probe 2), are used to screen the library simultaneously. Only clones which hybridize with both probes are selected, thus minimizing the number of potential false positive clones which will need to be sequenced to identify the correct clones. Approximately $10^6$ independent recombinant clones are screened using the radiolabeled probes described above on duplicate lifts of filters from the from the library as described by Benton, et al., Science 196:180–2 (1977). Bacterial colonies from the plasmid library are also screened using the method described by Grunstein et al., Proc. Natl. Acad. Sci. 72:3961 (1975). The first filter lift from each plate is probed with radiolabelled probe 1, and the second filter lift is probed with radiolabelled probe 2. Only those clones which hybridize with both probes are subjected to second and third round screening and enrichment, until a purified population of clones, 100% of which hybridize with the probes, is obtained.

Each of the clones is characterized for relatedness by the criteria of restriction endonuclease mapping, insert size, and cross-hybridization. The ultimate identity of the correct clone is determined by nucleotide sequence analysis. Clones with open reading frames which encode proteins having sequence homology with the polypeptides of the present invention are the appropriate clones, and are suitable for use in expression vectors.

All publications and other references or patent documents herein described are incorporated by reference. It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed is:

1. A polynucleotide encoding the polypeptide comprising the amino acid sequence designated SEQ ID No:1.

2. The polynucleotide of claim 1, wherein the polypeptide has a molecular weight of approximately 20 kD.

3. The polynucleotide of claim 1, which is contained in an expression vector suitable for expressing the polypeptide in a procaryotic or eucaryotic host.

4. A host cell containing the polynucleotide of claim 3 and capable of expressing the encoded polypeptide.

5. A method for producing a polypeptide comprising SEQ. ID. No. 1 and capable of inhibiting an integrin-mediated adhesion of a mammalian cell, comprising culturing a host cell of claim 4 under conditions suitable for expression of said polypeptide.

6. The polynucleotide of claim 1, wherein the polypeptide has a molecular weight of approximately 4 kDa.

7. The polynucleotide of claim 2, wherein the amino acid sequence SEQ ID No:1 is present at the amino terminal of the polypeptide.

* * * * *